United States Patent
Luukkainen

(10) Patent No.: US 7,926,488 B2
(45) Date of Patent: Apr. 19, 2011

(54) FRAME OF AN INTRAUTERINE SYSTEM

(75) Inventor: Tapani Luukkainen, Espoo (FI)

(73) Assignee: Familplan Consulting Ltd. Oy, Vantaa (FI)

( * ) Notice: Subject to any disclaimer, the term of this patent is extended or adjusted under 35 U.S.C. 154(b) by 710 days.

(21) Appl. No.: 11/004,867

(22) Filed: Dec. 7, 2004

(65) Prior Publication Data

US 2005/0126575 A1 Jun. 16, 2005

(30) Foreign Application Priority Data

Dec. 11, 2003 (EP) .................................. 03396112

(51) Int. Cl.
*A61F 6/06* (2006.01)
(52) U.S. Cl. ....................................... 128/833; 128/830
(58) Field of Classification Search .................. 128/830, 128/831, 832, 833
See application file for complete search history.

(56) References Cited

U.S. PATENT DOCUMENTS

| 3,757,775 | A | * | 9/1973 | Marco et al. ................... | 128/839 |
| 3,782,376 | A | * | 1/1974 | Lerner ............................ | 128/839 |
| 3,918,445 | A | * | 11/1975 | Okamoto et al. .............. | 128/840 |
| 3,935,860 | A | * | 2/1976 | Hoff ............................... | 128/839 |
| 3,952,734 | A | * | 4/1976 | Van Os et al. .................. | 128/840 |
| 4,578,076 | A |   | 3/1986 | Luukkainen et al. .......... | 604/892 |
| 5,417,223 | A | * | 5/1995 | Aarnio et al. .................. | 128/833 |

FOREIGN PATENT DOCUMENTS

| DE | 41 25 575 | 4/1995 |
| FR | 2 517 539 | 6/1983 |
| GB | 1 568 419 | 5/1980 |

* cited by examiner

*Primary Examiner* — Patricia M Bianco
*Assistant Examiner* — Camtu T Nguyen
(74) *Attorney, Agent, or Firm* — James C. Lydon

(57) ABSTRACT

A frame of an intrauterine system which includes an elongate member having at its first end a transverse member including a first wing and a second wing, first ends of the wings being attached to the elongate member. The first and second wings are symmetrically bent towards a second end of the elongate member so that an angle a formed between the elongate member and the first or second wing is 10°-60°. The second ends of the wings are symmetrically bent towards the elongate member by an angle β that is 40°-140°.

6 Claims, 3 Drawing Sheets

FRAME OF AN INTRAUTERINE SYSTEM

FIELD OF THE INVENTION

This invention relates to a frame of an intrauterine system consisting of an elongate member having at its first end a transverse member comprising a first wing and a second wing, first ends of said wings being attached to said elongate member.

BACKGROUND OF THE INVENTION

The publications and other materials used herein to illuminate the background of the invention, and in particular, the cases to provide additional details respecting the practice, are incorporated by reference.

Intrauterine systems (IUS) are well known in the art. For example, document GB 1 568 419 presents an intrauterine device that has a T-shaped frame. The arms of the frame are curved so that they will resist becoming embedded in the sidewalls of the fundus and the arms will flex under uterine contractions. In its preferred and only illustrated form, the device includes a formation adapted to resist movement into the cervical canal, said formation having the form of a pair of lugs extending away from the stem of the device.

Document U.S. Pat. No. 4,578,076 by the Applicant discloses intrauterine and intracervical devices that also have a T-shaped frame. The frame has a vertical stem portion with a rounded knob at the top of the vertical stem and two flat flexible downward slanting arms extending from the knob, the arms tapering from the knob to the ends of the arms and having a downward bend of about 45°-110° proximate the end of each arm. Furthermore, the arms slant down from the knob at an angle of about 10°-25°, when measured from the horizontal, i.e. the plane perpendicular to the longitudinal axis of the elongate member.

The problem that is addressed in these documents is the irritation of the endometrium and bleeding caused by the devices, which have the traditional T-shape, i.e. those in which the arms are not bent down towards the other end of the elongate member.

Document FR 81 22676 discloses a device that comprises three pairs of transverse members. Only one pair of these members is located at an end of the elongate member. The device also provides a large area of contact with the walls of the uterus, thus creating problems of bleeding and pain for the user. Furthermore, one end of the elongate member is provided with a half sphere having sharp edges. Such a sphere, especially with its sharp edges facilitates the intrusion of the device into the wall of the uterus, thus making the removal of the device highly difficult.

OBJECTS AND SUMMARY OF THE INVENTION

The object of this invention is to provide an alternative solution to the above-mentioned problem, i.e. to improve the intrauterine systems as follows:.
  to make insertion easy and safe by avoiding the perforations or penetrations of the uterine wall.
  to avoid the contact and the irritation of the endometrium and thus bleeding problems.
These objectives are achieved with the system as described in the appended independent claims.

The present invention relates to a frame of an intrauterine system consisting of an elongate member having at its first end a transverse member comprising a first wing and a second wing, first ends of said wings being attached to said elongate member, said frame being characterized in that said first and second wings are symmetrically bent towards a second end of said elongate member so that an angle $\alpha$ formed between said elongate member and said first or second wing is 10°-60° and in that the second ends of the wings are symmetrically bent towards the elongate member by an angle $\beta$ that is 40°-140°.

DETAILED DESCRIPTION OF THE INVENTION

The invention is disclosed in the appended claims.

The device according to the invention is characterized in that said first and second wings are symmetrically bent towards a second end of said elongate member so that an angle ax formed between said elongate member and said first or second wing is 10°-60° and in that the second ends of the wings are symmetrically bent towards the elongate member by an angle $\beta$ that is 40°-140°.

Thus, the invention concerns a frame of an intrauterine system wherein the arms of a T-shaped frame are bent down towards the other end of the elongate member of the frame. Furthermore, the free ends of the arms of the T-shaped frame are also curved, so as to avoid irritation of the endometrium. The invention thus provides an alternative solution to the problem mentioned in prior art, as mentioned above. The present invention thus provides the improvements listed above. Indeed, the system according to the present invention makes the insertion easy and safe by avoiding the perforations or penetrations of the uterine wall. The training of the insertion being a problem in the use of IUS's, this problem is also at least partially solved by the system according to the invention, because its insertion needs minimal training, thus making mass-use possible.

Moreover, the IUS according to the present invention avoids the contact with and irritation of the endometrium and thus bleeding problems The angle $\alpha$ is defined as the angle formed between said elongate member and said first or second wing, i.e. differently from the angle mentioned in U.S. Pat. No. 4,578,076.

According to an embodiment of the invention, said angle $\alpha$ is 20°-50°, preferably 30°-500. It is however clear to a person skilled in the art, that the angle $\alpha$ may be for example also in the range of 10°-50°, 10°-45°, 15°-60°, 15°-55°, 17°-45°, 25°-45°, 30°-60° or 45°-60°.

According to another embodiment of the invention, said angle $\beta$ is 60°-130°, preferably 90°-120°. However, a person skilled in the art readily knows that said angle $\beta$ may also be for example in the range of 40°-70°, 50°-120°, 57°-125°, 60°-135°, 79°-110°, 90°-140°, 110°-137° or 120°-140°.

The elongate member of a frame according to the present invention preferably further has a rounded knob at its first end and said first and second wings are typically attached to said knob.

The frame according to the present invention is also preferably provided with a opening at the second end of the elongate member, wherein a thread may be attached, said thread being used for removing the IUS and indicating its presence in the uterine cavity.

Moreover, the frame of the system according to the present invention is designed to carry a therapeutically active agent, i.e. a drug, reservoir. Such a reservoir may be any reservoir known in the art.

The device according to the present invention, i.e. the frame of an intrauterine system, therefore typically comprises also one or more systems having the desired therapeutical effect. Said system may be for example metal wire, such as a copper wire, or a frame made of an elastomer and comprising a therapeutically active agent. Such bodies comprising therapeutically active agents have been disclosed in the prior art. This system(s) is preferably positioned on the elongate member of the frame, but it may also be positioned in one or both of the wings.

The frame according to the present invention, optionally additioned by a system as described above, may be inserted by means of a conventional inserter. The wings of the frame may be left outside the inserter during the insertion.

The frame according to the present invention is typically approximately 3 cm in length, for example from 2,2 to 4,5 cm long. The cross-section of the elongate member is typically from 0,5 to 5 mm and the length of the wings is typically from 0,8 to 1,7 cm.

The invention still relates to a method of medication wherein a system capable of releasing at least one therapeutically active agent is arranged on a frame of an intrauterine system according to the present invention, thereby forming an intrauterine system, said intrauterine system is introduced to the uterine cavity of a patient and positioned therein for the period of time the medication is desired. Said period of time may be several years, even up to ten years. In this description, by medication, also contraception is meant.

In this specification, except where the context requires otherwise, the words "comprise", "comprises" and "comprising" means "include", "includes" and "including", respectively. That is, when the invention is described or defined as comprising specified features, various embodiments of the same invention may also include additional features. Also, the reference signs should not be construed as limiting the claims.

The invention is described below in greater detail by the following, non-limiting drawing.

DETAILED DESCRIPTION OF THE DRAWING

Figure 1:
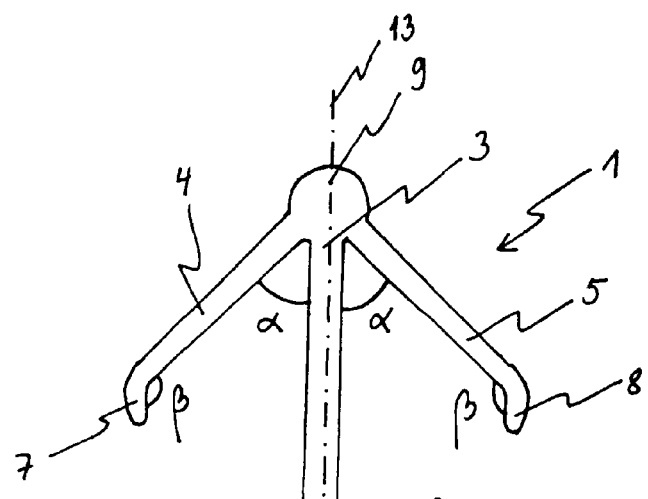
FIG. 1 illustrates a frame of an intrauterine system according to a first embodiment of the invention.

FIG. 1 illustrates a frame of an intrauterine system according to a first embodiment of the invention. The frame 1 comprises an elongate member 2 having at its first end 3 a transverse member comprising a first wing 4 and a second wing 5 attached to said elongate member 2. The first and second wings 4, 5 are bent towards a second end 6 of said elongate member 2 so that the angle $\alpha$ formed between said elongate member 2 and said first or second wing 4, 5 is 47°. The second ends 7, 8 of said wings 4, 5, i.e. the ends that are not attached to said elongate member 2, are bent towards said elongate member 2, so that the angle $\beta$ is 135°.

The first end 3 of the elongate member 2 is further provided with a rounded knob 9, and the second end of the elongate member 2 is provided with an opening 10 for attaching a thread 11. In this embodiment, as in the other embodiments, the frame 1 is symmetrical with respect to the longitudinal axis 13 of the elongate member 2.

Figure 2:
FIG. 2 illustrates a frame of an intrauterine system according to a second embodiment of the invention.
Figure 2:
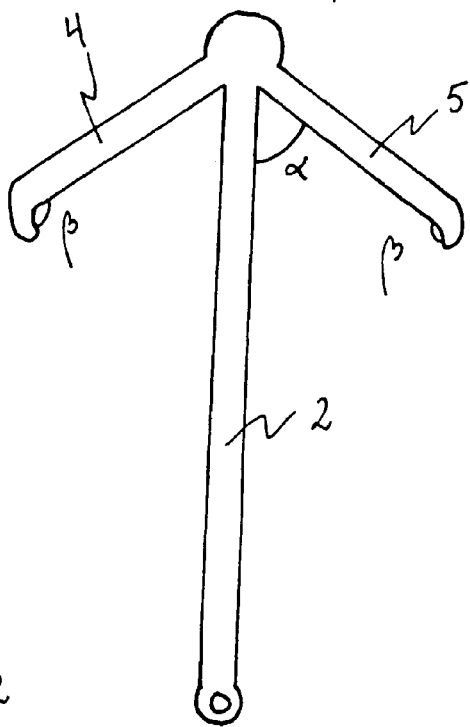

FIG. 2 illustrates a frame of an intrauterine system according to a second embodiment of the invention. This second embodiment is otherwise identical to the first embodiment, except that the angle $\alpha$ formed between said elongate member 2 and said first or second wing 4, 5 is 55° and the angle $\beta$ is 110°.

Figure 3:
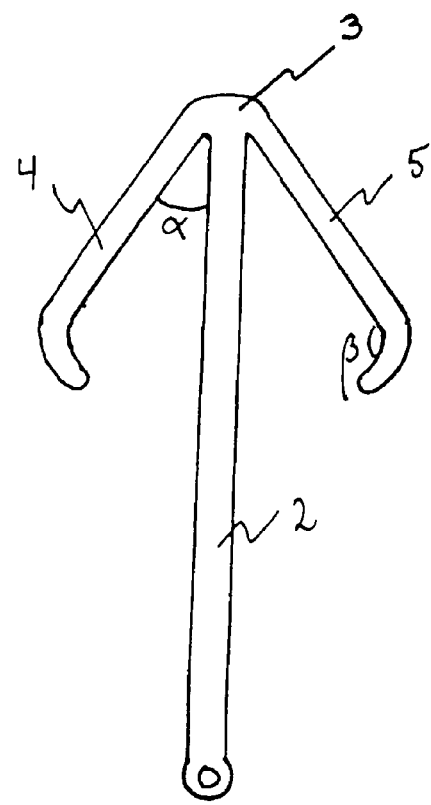
FIG. 3 illustrates a frame of an intrauterine system according to a third embodiment of the invention.

FIG. 3 illustrates a frame of an intrauterine system according to a third embodiment of the invention. In this embodiment, the first end 3 of the elongate member 2 is not provided with a knob. The angle $\alpha$ formed between said elongate member 2 and said first or second wing 4, 5 is 38° and the angle $\beta$ is 116°.

Figure 4:
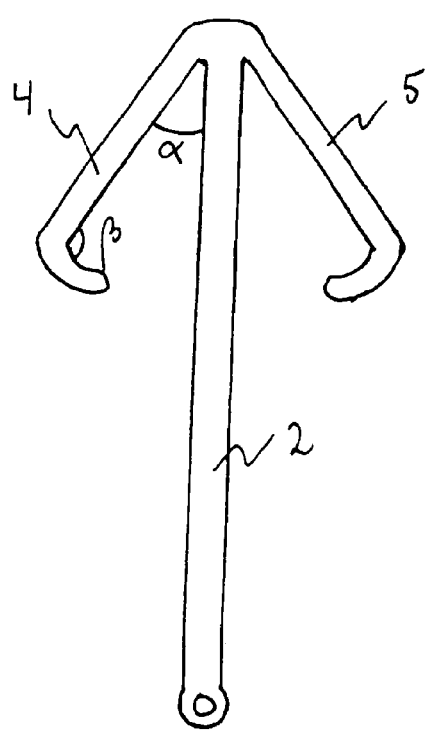
FIG. 4 illustrates a frame of an intrauterine system according to a fourth embodiment of the invention.

FIG. 4 illustrates a frame of an intrauterine system according to a fourth embodiment of the invention. This embodiment is otherwise identical to the third embodiment except that the angle $\beta$ is 90°. The angle $\alpha$ is 38° as in the third embodiment.

Figure 5:
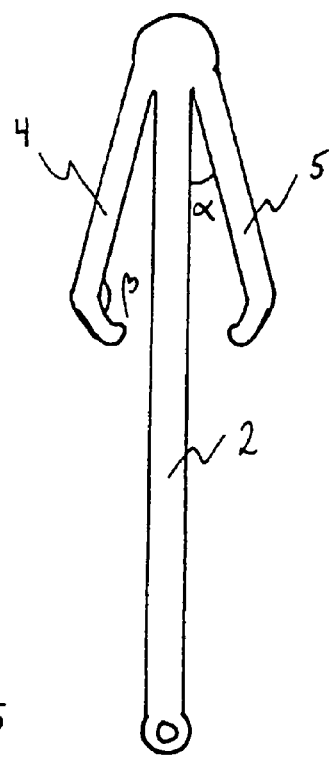
FIG. 5 illustrates a frame of an intrauterine system according to a fifth embodiment of the invention.

FIG. 5 illustrates a frame of an intrauterine system according to a fifth embodiment of the invention. In this embodiment, the angle $\alpha$ formed between said elongate member 2 and said first or second wing 4, 5 is 15° and the angle $\beta$ is 136°.

Figure 6:
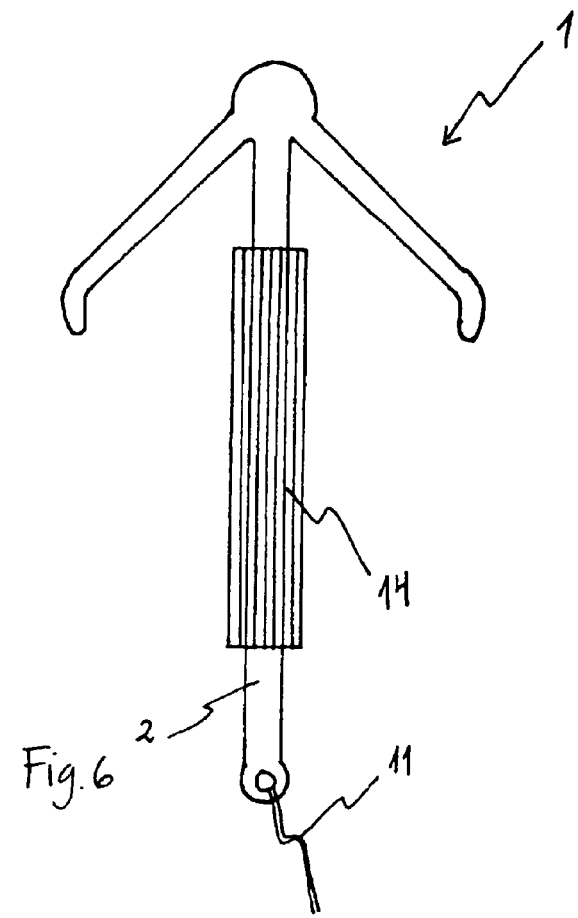
FIG. 6 illustrates an intrauterine system according to a sixth embodiment of the invention.

FIG. 6 illustrates an intrauterine system, wherein to a frame 1 according to the first embodiment of the invention, illustrated in FIG. 1, a delivery system 14 is positioned on the elongate member 2. The delivery system 14 is here a system consisting of an elastomer and a therapeutically active agent. The Figure further shows a thread 11 attached to the frame, i.e. the device is ready for use.

The invention claimed is:

1. A frame of an intrauterine system comprising an elongate member having at its first end a transverse member comprising a first wing and a second wing only, first ends of said wings being attached to said elongate member, wherein said first and second wings are symmetrically bent towards a second end of said elongate member so that an angle $\alpha$ formed between a longitudinal axis of said elongate member and said first or second wings is 10°-60° and wherein the second ends of the wings are symmetrically bent towards the elongate member by an angle $\beta$ of 40°-140°.

2. The frame of claim 1, wherein said angle $\alpha$ is 20°-50°.

3. The frame of claim 2, wherein said angle $\alpha$ is 30°-50°.

4. The frame of claim 1, wherein said angle $\beta$ is 60°-130°.

5. The frame of claim 4, wherein said angle $\beta$ is 90°-120°.

6. The frame of claim 1, wherein its elongate member further has a rounded knob at its first end wherein said first and second wings are attached to said knob.

* * * * *